United States Patent [19]

Shigematsu et al.

[11] Patent Number: 4,735,972
[45] Date of Patent: Apr. 5, 1988

[54] THERMOPLASTIC RESIN COMPOSITION

[75] Inventors: Akira Shigematsu; Kunio Suzuki, both of Hyogo, Japan

[73] Assignee: Daicel Chemical Industries, Ltd., Osaka, Japan

[21] Appl. No.: 899,852

[22] Filed: Aug. 25, 1986

[30] Foreign Application Priority Data

Nov. 15, 1985 [JP] Japan .............................. 60-256430
Apr. 23, 1986 [JP] Japan .............................. 61-94079

[51] Int. Cl.$^4$ .......................... C08K 3/30; C08K 3/24
[52] U.S. Cl. .................................. 523/102; 524/423
[58] Field of Search ...................... 523/102; 524/423

[56] References Cited

U.S. PATENT DOCUMENTS

| | | | |
|---|---|---|---|
| 2,785,146 | 3/1957 | Davies et al. | 524/423 |
| 3,951,894 | 4/1976 | Whelan | 524/423 |
| 3,997,502 | 12/1976 | Schaupp | 524/423 |
| 4,055,538 | 10/1977 | Kroenke | 524/423 |

FOREIGN PATENT DOCUMENTS

| | | | |
|---|---|---|---|
| 2403546 | 8/1975 | Fed. Rep. of Germany | 524/423 |
| 50-25652 | 3/1975 | Japan | 524/423 |
| 56-20055 | 2/1981 | Japan | 523/102 |

*Primary Examiner*—Lewis T. Jacobs
*Attorney, Agent, or Firm*—Sughrue, Mion, Zinn, Macpeak, and Seas

[57] ABSTRACT

A thermoplastic resin composition having deodorizing properties, which is obtained by adding to a thermoplastic resin from 0.5 to 100% by weight of fine powders of ferrous sulfate having a total content of crystal water and free water of not more than 20% by weight or fine powders of aluminum sulfate, potassium aluminum sulfate, sodium aluminum sulfate or zinc sulfate having a total content of crystal water and free water of not more than 5% by weight, and kneading the mixture and/or molding the mixture. The composition can be processed at high temperatures and does not undergo color change with time.

9 Claims, No Drawings

THERMOPLASTIC RESIN COMPOSITION

FIELD OF THE INVENTION

This invention relates to a thermoplastic resin composition having a deordorizing property.

BACKGROUND OF THE INVENTION

Removal of a bad odor emitted in a living environment has been one of the great subjects in pursuit of comfort. It is known that bad odors can be removed or destroyed through various mechanisms, such as masking, adsorption, neutralization, and the like, and a wide variety of deodorizers or deodorants utilizing these mechanisms are now on the general market.

On the other hand, thermoplastic resin products have now thoroughly penetrated into our daily life and been widely used. Therefore, the thermoplastic resin molded products are broadly employed as containers for the deodorizers. However, thermoplastic resin products having deodorizing properties in themselves are rarely known.

Deodorizers are classified by deodorizing mechanism into two large groups, one by adsorption and the another by chemical reaction. The reactive deodorizers produce rapid and powerful effects on some specific sources of bad odors. For example, it is known that ferrous sulfate can remove ammonia and the reaction product between ferrous sulfate and ammonia is capable of removing ammonia and hydrogen sulfide, respectively, as disclosed in Japanese Patent Publication No. 6698/55 and Japanese Patent Application (OPI) No. 50889/76 (the term "OPI" as herein used means "unexamined published application"). The deodorizing mechanism by these compounds is admittedly assumed to follow the following reactions:

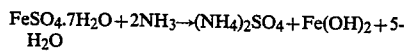

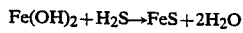

It has been recognized by recent studies that these deodorizers can exert their deodorizing performance through the above-described mechanism even when blended with thermoplastic resins.

However, divalent iron compounds tend to be gradually oxidized under ambient conditions to form an iron rust smell and iron rust-colored stain which contaminate materials in contact therewith. It is also known to use ascorbic acid in combination for the purpose of stabilizing the divalent iron compounds, but ascorbic acid cannot be expected to show its effects after molding because it is generally decomposed at molding temperatures of thermoplastic resins.

SUMMARY OF THE INVENTION

An object of this invention is to provide a thermoplastic resin composition having functions, such as deodorizing, which can be processed at high temperatures and do not undergo color change with time.

As a result of extensive investigations for the purpose of accomplishing the above object, it has now been found that a thermoplastic resin composition which possesses both the deodorizing function and the functions inherent to the resin and suffers neither coloration upon processing nor color change with time can be obtained by incorporating, as a deodorizing component, fine powders of ferrous sulfate containing crystal water and free water in a total amount of not more than 20% by weight or fine powders of aluminum sulfate, potassium aluminum sulfate, sodium aluminum sulfate or zinc sulfate containing crystal water and free water in a total amount of not more than 5% by weight into a thermoplastic resin. The present invention has been completed based on this finding.

The functions such as deodorizing function are effectively exhibited particularly when molded into a molded article having a large specific surface area, such as, for example, a bag for garbage disposal.

The above-described deodorizing components are not well miscible with thermoplastic resins. In order to solve this problem, the inventors have found it advantageous to prepare a master batch containing these components in high concentrations, which is mixed with a molding resin at a prescribed ratio upon molding.

Accordingly, it is another object of this invention to provide a master batch containing the deodorizers in a good dispersed state at high concentrations.

That is, the present invention relates to a thermoplastic resin composition having deodorizing properties, which is obtained by adding to a thermoplastic resin from 0.5 to 100% by weight of fine powders of ferrous sulfate containing crystal water and free water in a total amount of not more than 20% by weight or fine powders of aluminum sulfate, potassium aluminum sulfate, sodium aluminum sulfate or zinc sulfate containing crystal water and free water in a total amount of not more than 5% by weight, and kneading the mixture and/or molding the mixture.

DETAILED DESCRIPTION OF THE INVENTION

Ferrous sulfate obtainable by a usual process and commercially available is a heptahydrate. When ferrous sulfate hepthydrate is mixed with a thermoplastic resin and heated to a melting temperature of the resin, e.g., 130° C., part of crystal water is released and gasified to cause foaming. Under such a condition, satisfactory molded products cannot be obtained. Even if a resin having a low melting point is selected and the molding is completed in a short time, ferrous sulfate heptahydrate is susceptible to oxidation by oxygen and moisture in air to be converted to ferric sulfate or ferric hydroxide, readily resulting in color change or effect reduction.

When ferrous sulfate heptahydrate is dried by heating at about 120° C., it loses substantially most of the crystal water to become a monohydrate, which does not lose crystal water any more under usual conditions for molding thermoplastic resins, thus causing no foaming upon molding. In addition to the susceptibility to oxidation as mentioned above, ferrous sulfate heptahydrate is not only hygroscopic but also very poor in miscibility with hydrophobic resins. To make a contrast, the monohydrate has high resistance to oxidation and moisture absorption and satisfactory miscibility with hydrophobic resins.

Since ferrous sulfate is hydrophilic, it usually has adorbed thereto so-called free water in addition to crystal water. As it is recognized that all the moisture content of ferrous sulfate is removed by heating at 300° C. for about 1 hour, a total content of crystal water and free water is defined as a weight loss on heating at 300° C. for 1 hour.

When the thus defined total content of crystal water and free water is not more than 20% by weight, and preferably not more than 15% by weight, it is considered that the major part of ferrous sulfate exists in the form of monohydrate, with a part being present in the form of tetrahydrate. Such ferrous sulfate can be used advantageously to fulfil the object of this invention.

The ferrous sulfate to be used in the present invention should be fine powders. As the particle size becomes smaller, the disadvantages in molding processing are mitigated, and the deodorizing capacity is enhanced with increase of specific surface area. In the particular case of applying the composition of the invention to bas for garbage disposal, a particle size of not greater than 30 μm is preferred. Such fine powders of ferrous sulfate can suitably be obtained by grinding ferrous sulfate, followed by sieving.

Deodorizers which can be used in the present invention other than the above-described ferrous sulfate are aluminum sulfate, aluminum sulfate double salts except for ammonium aluminum sulfate, such as potassium aluminum sulfate and sodium aluminum sulfate, and zinc sulfate, any of which is capable of removing bad odors of ammonia gas similarly to the ferrous sulfate.

The most stable form of aluminum sulfate, potassium or sodium aluminum sulfate or zinc sulfate is an octadecahydrate, a dodecahydrate or a heptahydrate, respectively. When commercially available products of these compounds containing a slight amount of absorbed free water in addition to the crystal water are mixed thermoplastic resins and heated to a molding temperature, the moisture content is released and gasified to cause irregular foaming in the resin as in the case of ferrous sulfate heptahydrate. Further, the deodorizers per se undergo unfavorable phenomena, such as re-dissolution and cohesion.

Apart from these hydrates, aluminum sulfate free from crystal water or a double salt thereof is commercially available under the name of anhydrous aluminum sulfate or burnt alum. These anhydrous salts tend to absorb moisture in air when stored under usual conditions. It is considered that the absorbed water is in the state of free water, or a part of it may be crystal water.

If the total content of free water and crystal water, being defined as a weight loss on heating at 300° C. as described above, is 5% by weight or less based on the salt used, the resulting resin composition fulfils the object of the present invention without inducing unfavorable phenomena, such as foaming, cohesion, and the like, under molding conditions generally employed for thermoplastic resins.

It is desirable that the anhydrous aluminum sulfate or burnt alum be used in the form of fine powder so as to have a large specific surface area as possible. In particular, when the resin composition is molded into films, the particle size should be less than the film thickness, i.e., 30 μm or less.

Anhydrous zinc sulfate which can also be used as a deodorizer in the present invention is less hygroscopic and more stable than anhydrous aluminum sulfate. The same conditions for incorporation into resins and molding as for anhydrous aluminum sulfate can be applied to anhydrous zinc sulfate.

The thermoplastic resins which can be used in the present invention are not particularly limited as long as they can be injection molded or extrusion molded. Examples of employable resins include polyolefin resins, e.g., polyethylene, polypropylene, polystyrene, etc., vinyl resins, e.g., polyvinyl chloride, polyvinylidene chloride, polymethyl methacrylate, etc., cellulose resins, e.g., cellulose acetate, etc., polyamide resins, polyester resins, diene elastomers, e.g., polybutadiene, polyisoprene, etc., copolymer resins, e.g., ethylene-vinyl acetate copolymers, styrene-acrylonitrile copolymers, styrene-butadiene-acrylonitrile copolymers, etc., and the like.

These resins are fed to a molding machine in the form of powders, beads, granules, etc. and molded under heat and pressure. In carrying out molding, a molding compound in which the resin and the deodorizer according to the present invention are dispersed with sufficient uniformity can be prepared by mixing these components in a blender, melt-kneading the mixture in a plastomill, a kneader, a roll, an extruder, etc., molding the mixture into a plate or rod, which is then pelletized. Alternatively, master batch pellets comprising the deodorizer of the present invention at a high concentration may be prepared, which can be fed to a molding machine together with resin pellets.

In order to enjoy the expected deodorizing performance combined with the functions inherent to the thermoplastic resin, the content of the deodorizer according to the present invention in the final resin molded products ranges from 0.5 to 30% by weight based on the thermoplastic resin.

To this effect, the master batch to be molded can contain the deodorizer in high concentrations, e.g., in amounts of from 10 to 100% by weight based on the thermoplastic resin.

In the preparation of the master batch, in order to ensure satisfactory dispersion of the deodorizers in resin compositions, the deodorizer particles are previously kneaded with a low molecular weight resin having a molecular weight of from 1,500 to 60,000 to coat their surface with said resin. The resin-coated particles of the deodorizer are then blended with a molding resin, and the mixture is then pelletized in a pelletizer to prepare master batch pellets. The low molecular weight resin is preferably used in an amount one fifth to 10 times the weight of the deodorizer particles.

The low molecular weight resin to be used for coating the deodorizer particles and the molding resin may not be the same and may have slightly different compositions as long as sufficient compatibility can be assured. The reason of using the low molecular weight resin is that it has higher flowability as compared with the molding resin, thus enabling thorough kneading. However, too a small molecular weight reduces the viscosity too low, rather resulting in difficulty in mixing with the deodorizers of the invention that have a higher specific gravity than the resin.

The resin composition according to the present invention can contain, if desired, other additives commonly employed for thermoplastic resins, such as antioxidants, colorants, ultraviolet light absorbents, antistatics, flame-retardents, lubricants, and the like.

In the present invention, the term "thermoplastic resin composition" as used throughout the specification and claims includes both molding resins and molded products produced therefrom.

According to the present invention, the deodorizer selected from aluminum sulfate, potassium or sodium aluminum sulfate and zinc sulfate reacts with ammonia to remove its bad odor in accordance with the same mechanism as accounted for the reaction between ferrous sulfate and ammonia or the reaction between a reaction product of ferrous sulfate and ammonia and hydrogen sulfide. The deodorizing thermoplastic resin composition of the invention can be obtained by adding fine powders of the above-described deodorizer to a thermoplastic resin and kneading the mixture and/or molding the mixture.

Conventional solid deodorizers comprise a porous or gel matix on or in which a substance having deodorizing properties is carried or incorporated, and such a dense and continuous structure as thermoplastic resin molded products is rarely found. In the resin molded products according to the present invention, also, the particles of the deodorizer that can actually exert the deodorizing effects are assumed to be limited to those exposed on the surface of the molded products and those which are present in the vicinity of the surface and are thereby coated with a thin resin layer. The exposed particles are dissolved out by washing with water, whereas the resin-coated particles react with an odor-emitting gas diffusing into the resin layer without being dissolved out by washing with water. Although such particles beneath the thin resin layer are inferior to the exposed particles in instantaneous deodorizing performance, they are expected to have long-lasting effects and also high resistance to inactivation due to oxidation with oxygen in air.

The resin composition in accordance with the present invention can be applied to bags for garbage disposal, cushioning sheets, and the like, taking advantage of its deodorizing effects. For example, bags for garbage disposal produced by mixing a master batch containing 20% by weight of ferrous sulfate with a polyethylene resin and molding the resulting compound by blown-film extrusion do not substantially give off a bad odor of the garbage contained therein. Therefore, use of such bags in a kitchen greatly contributes to an improvement of a living environment. Further, the molding compound can be expansion-molded in a known manner to obtain a foamed sheet, which can be used as a cushioning material having a deodorizing function. Other deodorizers of the resent invention, such as aluminum sulfate and its double salts and zinc sulfate, can also be applied in the same manner as described above to exert their deodorizing function. Besides, the aluminum sulfate and its double salts and zinc sulfate are advantageous in that the resin compositions containing them are free from coloration upon processing or color change with time during preservation.

As described above, the thermoplastic resin composition of the present invention can be molded into shape-retaining products which combine the functions of deodorizers and of plastics.

Further, since the master batch according to the present invention contains the deodorizer in a high concentration, it may be used as such as a solid deodorizer.

The thermoplatic resin composition of the present invention has various functions in addition to the above-described deodorizing function. One of the so far confirmed functions is to decompose free chlorine in water. For example, when tap water containing free chlorine for sterilization is put in a container made of the thermoplastic resin composition containing ferrous sulfate particles of the present invention, the free chlorine is rapidly decomposed thereby to alter tap water to palatable one.

This invention will now be illustrated in greater detail with reference to the following examples, but it should be understood that they are not intended to limit the present invention. In these examples, all the parts and percents are given by weight unless otherwise indicated.

EXAMPLE 1

Commercially available ferrous sulfate heptahydrate was dried in vacuo at 120° C. for 2 hours to obtain powders having a total content of crystal water and free water of 13.9%. The powders were finely pulverized by the use of a pulverizer (ACM-10 Model, produced by Hosokawa Tekko K.K.) to a mean particle size of 8.6 $\mu$m with a maximum particles size being 30 $\mu$m. To 40 parts of the resulting fine particles were added 19 parts of a low molecular weight polyethylene wax having an average molecular weight of about 5,000 and a density of 0.93 g/cm$^3$ and 1 part of tetrakis[methylene-3-(3', 5'-di-t-butyl-4'-hydroxyphenylpropionate]methane, and the mixture was melt-kneaded at 120° C. in a three-roll mill to obtain wax-coated particles. The resulting wax-coated particles were mixed with 140 parts of a low density polyethylene powder having a density of 0.923 g/cm$^3$, a melt flow index of 7 g/10 min and a particle size below 20 mesh in a tumbling agitator and then melt-extruded in a single screw extruder under a reduced pressure of 350 Torr at a molten resin temperature of 130° C. to prepare polyethylene master batch pellets containing 20% of ferrous sulfate.

The deodorizing performance of the resulting master batch pellets per se was determined as follows.

Fifteen grams of the pellets were placed in a 9.7 liter-volume closed vessel containing 520 ppm of ammonia and 35 ppm of hydrogen sulfide. Gas concentrations after 4 hours' standing were measured by means of a detector tube. The above gas concentrations initially set approximately to levels of the atmosphere of raw sewage. As a result, the percents removal of ammonia and hydrogen sulfide by the master batch pellets were found to be 95% and 88%, respectively.

COMPARATIVE EXAMPLES 1 AND 2

In an attempt of preparing a master batch, the same procedure as described in Example 1 was repeated but replacing the fine powders of ferrous sulfate as used in Example 1 with fine powders of commercially available ferrous sulfate heptahydrate having a total content of crystal water and free water of 46.4% (Comparative Example 1) or the above-described fine powders having been hot-air dried at 60° C. for 24 hours so as to have a total content of crystal water and free of 32.5% (Comparative Example 2). However, in the step of kneading with the polyethylene wax, vigorous foaming occurred, resulting in the failure of obtaining a wax-coated material.

EXAMPLE 2

To 1 part of the master batch pellets as obtained in Example 1 was added 9, 4 or 2.3 parts of the same low density polyethylene as used in Example 1, and the resulting molding compound was formed into a tubular film having a width of 200 mm and a thickness of 40 $\mu$m by means of a blown-film extrusion apparatus at a molten resin temperature of 140° C. and a cooling temperature of 80° C.. The content of ferrous sulfate in the resulting film was 2%, 4% or 6.7%, respectively.

Two grams of each of the resulting film products was placed in a 9.7 liter-volume closed vessel containing 90 ppm of ammonia, and the ammonia concentration after 4 hours was measured. As a result, the percent removal of ammonia by the film was found to be 75%, 90% or 94%, respectively.

COMPARATIVE EXAMPLE 3

Master batch pellets containing 20% of ferrous sulfate were prepared in the same manner as described in Example 1 but replacing the ferrous sulfate as used in Example 1 with ferrous sulfate having a total content of crystal water and free water of 10.6%, a mean particle size of 52 μm and a maximum particle size of 85 μm. A low density polyethylene film was produced in the same manner as described in Example 2 but using the above prepared master batch pellets. The resulting film suffered serious surface roughening but was free from pinholes. The percent removal of ammonia by this film as determined in the same manner as in Example 2 was 63% (ferrous sulfate content: 2%), 66% (ferrous sulfate content: 4%) or 68% (ferrous sulfate content: 6.7%), indicating inferiority to the corresponding film of Example 2.

EXAMPLE 3 AND COMPARATIVE EXAMPLE 4

To 37.5 parts of the same wax-coated particles as prepared in Example 1 were added 62.5 parts of ethylene-propylene copolymer pellets having an ethylene content of 3.3% and a melt flow index of 17 g/10 min, followed by mixing at 120° C. in a super mixer. After cooling, the blend was extruded in a single screw extruder at 170° C. under a reduced pressure of 150 Torr to prepare master batch pellets containing 25% of ferrous sulfate. To 1 part of the master batch pellets was added 6 parts of polypropylene pellets having a density of 0.90 g/cm$^3$ and a melt flow index of 5.5 g/10 min, and the resulting compound was formed into a tubular film having a width of 260 mm and a thickness of 40 μm using a blown-film extrusion apparatus at a molten resin temperature of 180° C. and a cooling temperature of 25° C. A bag having a depth of 470 mm was prepared from the resulting tubular film (Example 3). For comparison, a bag of the same size was prepared in the same manner but using no ferrous sulfate (Comparative Example 4).

Into each of the bags, 500 g of garbage was put, and the bag with its opening sealed was left to stand outdoors in the autumn sun. Two hours later, the openings of the two bags were opened to compare the odor. As a result, the bag containing ferrous sulfate scarcely smelled, while the bag containing no ferrous sulfate gave off a very strong smell.

EXAMPLE 4

To 1 part of the polyethylene master batch pellets as prepared in Example 1 was added 19 parts of polyethylene pellets having a density of 0.920 g/cm$^3$ and a melt flow index of 1.9 g/10 min, and the resulting molding compound was injection-molded at a molten resin temperature of 150° C. to produce a water bottle having a capacity of 650 cc and a weight of 85 g.

After the bottle was thoroughly washed with water, it was filled with tap water containing 0.7 ppm of free chlorine, and changes in free chlorine content with time at room temperature was determined. Thirty minutes later, the free chlorine content decreased to 0.1 ppm or less, and the water turned out to be palatable being free from the odor characteristic of a bleaching powder used in tap water.

EXAMPLE 5

Twenty parts of low molecular weight polyethylene having an average molecular weight of about 5,000 and a density of 0.93 g/cm$^3$ were added to 40 parts of commercially available anhydrous aluminum sulfate fine powders having a mean particle size of 5.8 μm and a maximum particle size of 28 μm (ignition loss at 300° C.: 1.3%), followed by melt-kneading at 120° C. in a three-roll mill to obtain wax-coated particles. To the wax-coated particles was added 40 parts of a low density polyethylene powder having a density of 0.923 g/cm$^3$, a melt flow index of 7 g/10 min and a particle size blow 20 mesh. The mixture was blended in a tumbling agitator and then extruded in a single screw extruder at a molten resin temperature of 140° C. to prepare polyethylene master batch pellets containing 40% of anhydrous aluminum sulfate.

The percent removal of ammonia by the resulting master batch pellets as determined in the same manner as in Example 1 was found to be 94%.

COMPARATIVE EXAMPLE 5

In an attempt of preparing a master batch, the same procedure as in Example 5 was repeated but replacing the anhydrous aluminum sulfate with commercially available dehydrated aluminum sulfate powders having an ignition loss at 300° C. of 26% and a particle size such that 75% or more of the powders passed through a 100 mesh. However, in the step of kneading with the polyethylene wax, cohesion of particles and foaming occurred, resulting in the failure of obtaining a uniformly dispersed coated material.

EXAMPLE 6 AND COMPARATIVE EXAMPLE 6

To 1 part of the master batch pellets prepared in Example 5 was added 9 parts of the same low density polyethylene as used in Example 5, and the resulting molding compound was formed into a tubular film having a width of 250 mm and a thickness of 30 μm by using a blown-film extrusion apparatus at a molten resin temperature of 150° C. and a cooling temperature of 80° C.

A bag having a depth of 470 mm was prepared from the resulting tubular film (Example 6). For comparison, a bag of the same size was prepared in the same manner as described above but using no anhydrous aluminum sulfate (Comparative Example 6). Into each bag was put 500 g of garbage, and the bag with its opening closed was left to stand outdoors in the autumn sun for 2 hours. After the standing, the openings of the bags were opened to compare odors.

As a result, the bag containing anhydrous aluminum sulfate scarcely smelled, while the bag containing no anhydrous aluminum sulfate gave off a very strong smell.

EXAMPLE 7

Commercially available burnt potash alum (potassium aluminum sulfate) having a mean particle size of 57 μm and a maximum particle size of 105 μm (ignition loss at 300° C.: 0.8%) was air-classified by the use of Micron Separator MS-1 Model (manufactured by Hosokawa Micron K.K.) to obtain fine particles having a mean particle size of 4.8 μm and a maximum particle size of 30 μm. The resulting fine particles were coated with a polyethylene wax in the same manner as in Example 5, and 70 parts of polypropylene powders having a density of 0.90 g/cm$^3$, a melt flow index of 5.5 g/10 min and a particle size blow 20 mesh were added thereto. After mixing in a tumbling agitator, the molding compound was extruded in a single screw extruder at a molten resin temperature of 250° C. to prepare polypropylene master batch pellets containing 20% of burnt potash alum.

To 1 part of the master batch pellets was added 9 parts or 4 parts of the same polypropylene pellets as used above in the preparation of the master batch. The resulting molding compound was molded into tubular film having a width of 200 mm and a thickness of 40 μm by the use of a blown-film extrusion apparatus at a molten resin temperature of 260° C. and a cooling temperature of 25° C. The burnt potash alum content in the film was 2% or 4%, respectively.

About 2 g (200 mm×300 mm) of the film was placed in a 9.7 liter-volume closed vessel containing 105 ppm of ammonia, and the ammonia concentration after 4 hours was measured by a detector tube. As a result, the percent removal of ammonia by the film was found to be 44% or 67%, respectively.

COMPARATIVE EXAMPLE 7

Master batch pellets containing 20% of burnt potash alum were prepared in the same manner as described in Example 7 but using unclassified burnt potash alum. Using the resulting master batch pellets, a polypropylene film having a burnt potash alum content of 2% or 4% was prepared in the same manner as in Example 7. The resulting film suffered remarkable surface roughening but was free from pinholes.

The percent removal of ammonia by this film as determined in the same manner as in Example 7 was 35% (burnt potash alum content: 2%) or 58% (burnt potash alum content: 4%), indicating inferiority to the results of Example 7.

EXAMPLE 8

Crystals of sodium alum (sodium aluminum sulfate) (dodecahydrate) were prepared from an aqueous solution of aluminum sulfate containing 8% of aluminum oxide which is commercially employed in purification of water (city water) and sodium sulfate decahydrate. The sodium alum crystals were preliminarily dehydrated and then burnt in an electric furnace at 300° C. to obtain anhydrous burnt sodium alum. The burnt sodium alum was crushed with a hammer, pulverized in a ball mill and air-classified to obtain fine powders having a mean particle size of 4.1 μm and a maximum particle size of 30 μm. Six parts of the burnt sodium alum fine powders and 94 parts of 48 mesh-passing polyethylene terephthalate powders having an intrinsic viscosity of 0.75 (in a 0.5% o-chlorophenol solution) were blended in a Henschel mixer and extruded in a single screw extruder at a molten resin temperature of 260° C. under a reduced pressure of 400 Torr to obtain pellets containing 6% of burnt sodium alum. The resulting pellets were molded by a hot press heated at 260° C. to obtain a sheet of 120 mm in width, 120 mm in length and 1 mm in thickness.

The sheet was placed in a 7 liter-volume closed vessel containing 90 ppm of ammonia, and the ammonia concentration after 4 hours was measured by means of a detector tube. The percent removal of ammonia was found to be 54%.

EXAMPLE 9

A commercially available anhydrous zinc sulfate powder (ignition loss at 300° C.: 1.5%) was further pulverized using Cosmomizer (manufactured by Nara Kikai Seisakusho K.K.) to obtain fine powders having a mean particle size of 2.3 μm and a maximum particle size of 22 μm. To 20 parts of the zinc sulfate fine powders were added 5 parts of a low molecular weight polyethylene wax having an average molecular weight of about 5,000 and a density of 0.91 g/cm$^3$, 0.5 part of calcium stearate, 0.5 part of magnesium stearate and 74 parts of low density polyethylene having a density of 0.923 g/cm$^3$, a melt flow index of 9 g/10 min and a mean particle size of 48 mesh, followed by mixing in a Henschel mixer for 2 minutes. The mixture was extruded in a single screw extruder at a molten resin temperature of 155° C. under a reduced pressure of 400 Torr to produce polyethylene master batch pellets containing 20% of anhydrous zinc sulfate.

One part of the resulting master batch pellets and 4 parts of the same low density polyethylene powder as used above were mixed and melt-kneaded in a Brabender mixer heated at 150° C. for 7 minutes to prepare a compound containing 4% of anhydrous zinc sulfate. The resulting compound was calendered to obtain a sheet of 120 mm in width, 120 mm in length and 1 mm in thickness. The sheet was placed in a 6.5 liter-volume closed vessel containing 120 ppm of ammonia, and the ammonia concentration after 4 hours was measured. As a result, the percent removal of ammonia was found to be 51%.

While the invention has been described in detail and with reference to specific embodiments thereof, it will be apparent to one skilled in the art that various changes and modifications can be made therein without departing from the spirit and scope thereof.

What is claimed is:

1. A thermoplastic resin composition having deodorizing properties, which comprises a polyolefin resin and from 10 to 100% by weight, based on the resin, of a deodorizer selected from the group consisting of fine powders of ferrous sulfate, aluminum sulfate, potassium aluminum sulfate, sodium aluminum sulfate, and zinc sulfate, with the provisions that the ferrous sulfate has a total content of crystal water and free water of not more tan 20%, and the aluminum sulfate, potassium aluminum sulfate, sodium aluminum sulfate, and zinc sulfate each have a total content of crystal water and free water of not more than 5% by weight.

2. The thermoplastic resin composition as in claim 1, wherein said deodorizer has a particle size of not more than 30 μm.

3. The thermoplastic resin composition as in claim 1, wherein the fine powders of said deodorizer are coated with a resin having a molecular weight of from 1,500 to 60,000.

4. The thermoplastic resin composition as in claim 3, wherein said resin having a molecular weight of from 1,500 to 60,000 is used in an amount one fifth to 10 times the weight of the deodorizer.

5. A thermoplastic resin molded product having deodorizing properties, which is obtained from a thermoplastic resin composition comprising a polyolefin resin and from 10 to 100% by weight, based on the resin, of a deodorizer selected from the group consisting of fine powders of ferrous sulfate, aluminum sulfate, potassium aluminum sulfate, sodium aluminum sulfate, and zinc sulfate, with the provisions that the ferrous sulfate has a total content of crystal water and free water of not more than 20%, and the aluminum sulfate, postassium aluminum sulfate, sodium aluminum sulfate, and zinc sulfate each have a total content of crystal water and free water of not more than 5% by weight.

6. The thermoplastic resin molded product as in claim 5, wherein said deodorizer is present in an amount of from 0.5 to 30% by weight based on the polyolefin resin.

7. The thermoplastic resin molded product as in claim 5, wherein said deodorizer has a particle size of not more than 30 $\mu$m.

8. The thermoplastic resin as claimed in claim 1, wherein said polyolefin resin is selected from the group consisting of polyethylene, polypropylene and polystyrene.

9. The thermoplastic molded product as claimed in claim 5, wherein said polyolefin resin is selected from the group consisting of polyethylene, polypropylene and polystyrene.

* * * * *